(12) United States Patent
Santos et al.

(10) Patent No.: US 8,575,111 B2
(45) Date of Patent: Nov. 5, 2013

(54) PHARMACEUTICAL COMPOSITIONS AND METHODS FOR TREATING ERECTILE DYSFUNCTION

(75) Inventors: Robson Augusto Souza dos Santos, Belo Horizonte-MG (BR); Ruben Dario Sinisterra Millan, Belo Horizonte-MG (BR); Frederic Jean Georges Frezard, Belo Horizonte-MG (BR); Andrey Christian da Costa Goncalves, Belo Horizonte-MG (BR); Rodrigo Araujo Fraga da Silva, Belo Horizonte-MG (BR)

(73) Assignee: Universidade Federal de Minas Garais-UFMG, Belo Horizonte (BR)

( * ) Notice: Subject to any disclaimer, the term of this patent is extended or adjusted under 35 U.S.C. 154(b) by 689 days.

(21) Appl. No.: 12/524,688

(22) PCT Filed: Jan. 24, 2008

(86) PCT No.: PCT/BR2008/000022
§ 371 (c)(1),
(2), (4) Date: Apr. 20, 2010

(87) PCT Pub. No.: WO2008/089532
PCT Pub. Date: Jul. 31, 2008

(65) Prior Publication Data
US 2010/0196452 A1    Aug. 5, 2010

Related U.S. Application Data

(60) Provisional application No. 60/897,510, filed on Jan. 26, 2007.

(51) Int. Cl.
*A61K 38/08* (2006.01)
*A61K 38/00* (2006.01)
*C07K 7/06* (2006.01)
*C07K 7/14* (2006.01)

(52) U.S. Cl.
USPC ............ 514/21.7; 514/1.1; 530/329; 530/316

(58) Field of Classification Search
USPC ......................... 514/1.1, 21.7; 530/329, 316
See application file for complete search history.

(56) References Cited

U.S. PATENT DOCUMENTS 6,538,144 B2 * 3/2003 Heitsch ........................ 549/60
2005/0069533 A1 * 3/2005 Millan et al. ............... 424/94.64

FOREIGN PATENT DOCUMENTS

WO   02/080910 A1   10/2002
WO   2007/000036 A2   1/2007

OTHER PUBLICATIONS

Sampaio Walkyria O et al: "The G protein-coupled receptor MAS is involved in the NO-releasing activity of angiotensin —(1-7)" Hypertension, Lippincott Williams & Wilkins, US, vol. 43, No. 6 (Jun. 1, 2004), p. 1351, XP009139836, ISSN: 0194-911X.

(Continued)

*Primary Examiner* — Daniel Sullivan
*Assistant Examiner* — Barbara Frazier
(74) *Attorney, Agent, or Firm* — Sughrue Mion, PLLC

(57) ABSTRACT

The present invention relates to the use of Ang-(1-7) and/or Ang-(1-7) receptor agonist and/or Ang (1-7) analogue in treating/restoring erectile dysfunction.

10 Claims, 10 Drawing Sheets
(5 of 10 Drawing Sheet(s) Filed in Color)

(56) References Cited

OTHER PUBLICATIONS

De Buhr I et al: "Arachidonic acid release from Mas-transfected COS cell can be stimulated by Ang-(1-7), Ang III and Ang IV not involving AT1 and AT2 receptors". Naunyn$_{13}$ Schmiedeberg's Archives of Pharmacilogy, Springer, Berlin, DE, vol. 365, No. suppl. 1, (Mar. 1, 2002), p. R69, XP009139833, ISSN: 0028-1298.

European Search Report dated Oct. 22, 2010 in European Application No. 08700472.7.

Santos, Robson A. S. et al, "Angiotensin-(1-7) is an endogenous ligand for the G protein-coupled receptor Mas" PNAS, Jul. 8, 2003, vol. 100, No. 14, pp. 8258-8263.

* cited by examiner

PHARMACEUTICAL COMPOSITIONS AND METHODS FOR TREATING ERECTILE DYSFUNCTION

This application is the National Stage of PCT/BR2008/000022 filed Jan. 24, 2008, which claims the benefit of U.S. Provisional Application No. 60/897,510 filed Jan. 26, 2007, the disclosure of which is incorporated herein by reference.

FIELD OF THE INVENTION

The present invention relates to the use of Angiotensin-(1-7), alone or in combination with other therapeutic agents in treating erectile dysfunction (ED). Methods for treating ED and/or to restore erectile capacity are based on the use of Angiotensin-(1-7) alone or in combination with other therapeutic agents are also provided.

BACKGROUND OF THE INVENTION

Impotence or erectile insufficiency is a widespread disorder that is thought to affect about twelve percent of adult men under age forty-five, about twenty percent of men at age sixty, and about fifty-five percent of men at age seventy-five. A number of causes of erectile insufficiency, in addition to anatomical deficiencies of the penis or scrotum that preclude an erection sufficient for vaginal penetration, have been identified. These causes are psychological and physical in origin and in any individual suffering from impotence there may be more than one cause of erectile dysfunction.

Erectile dysfunction can be psychological, resulting, for example, from anxiety or depression, with no apparent somatic or organic impairment. Such erectile dysfunction, which is referred to as "psychogenic", is responsible for about fifteen to twenty percent of cases of impotence. In other cases, the erectile dysfunction is associated with atherosclerosis of the arteries supplying blood to the penis; such dysfunction is referred to as "arteriogenic" or "atherosclerotic." About forty to sixty percent of cases of impotence are arteriogenic in origin.

In still other cases, there is leakage from veins in the penis such that sufficient pressure for an erection can be neither obtained nor maintained. This dysfunction is referred to as "venous leakage," or "abnormal drainage". This condition is often exacerbated by the presence of some arteriogenic dysfunction whereby the supply of blood to the penis is impaired. In still other cases, the dysfunction is associated with a neuropathy, such as nerve damage arising from, for example, surgery or a pelvic injury, in the nervous system affecting the penis. Such a dysfunction is referred to as "neurogenic" and about ten to fifteen percent of cases of impotence are neurogenic in origin.

There is also a high incidence of erectile insufficiency among diabetics, particularly those with insulin-dependent diabetes mellitus. Erectile dysfunction in diabetics is often classified as "diabetogenic," although the underlying dysfunction is usually neurogenic associated with neuropathy, but may be arteriogenic or neurogenic and arteriogenic. About half of diabetic males suffer from erectile insufficiency, and about half of the cases of neurogenic impotence are in diabetics.

Erectile insufficiency is sometimes a side effect of certain drugs, such as beta-blockers that are administered to reduce blood pressure in persons suffering from hypertension, or drugs administered to treat depression or anxiety. Excessive alcohol consumption has also been linked to erectile insufficiency. These forms of erectile insufficiency may be regarded as a subset of neurogenic or psychogenic insufficiency.

A number of methods to treat impotence are available. These treatments include pharmacological treatments, surgery and, in cases of psychogenic dysfunction, psychological counseling is sometimes effective.

In the rare cases, where the insufficiency is untreatable because of venous leakage, surgery can usually be employed to repair the venous lesion and thereby either cure the insufficiency or, if there remains an erectile insufficiency after repair of the venous lesion, render the insufficiency amenable to treatment by pharmacological methods. Also, penile implants, which provide a mechanic means to produce an erection sufficient for vaginal penetration, are widely used to treat impotence. In recent years, implants have been employed, especially in cases where pharmacological intervention is ineffective, which are usually cases of severe atherogenic impotence. Treatment of impotence with penile implants, however, entails serious disadvantages. Such treatment requires surgery and necessitates total destruction of the erectile tissues of the penis, forever precluding normal erection.

Pharmacological methods of treatment are also available. Such methods, however, have not proven to be highly satisfactory or without potentially severe side-effects.

VIAGRA® (sildenafil citrate, Pfizer, Inc., New York, N.Y.), taken orally, is effective for up to 80% (depending upon the severity of erectile dysfunction (ED) and/or any underlying disease) of patients to produce an adequate erection for sexual intercourse. It is effective for a broad range of causes. Successful VIAGRA® patients have normal, natural erections. VIAGRA® has no effect on libido (sexual desire) so that it will not be effective unless a man feels stimulated.

VIAGRA® suppresses the enzyme phosphodiesterase so that the erection-producing chemical cyclic guanosine monophosphate (cGMP) is not broken down, so that a normal erection occurs. cGMP is a natural vasodilator (dilates penile arteries) which relaxes the smooth muscle of penile arteries so that the relaxed smooth muscle, in combination with normal blood pressure, causes the penile arteries to dilate so that the erectile chambers are engorged with blood to produce an erection.

Men who cannot take VIAGRA® or find it ineffective are often able to achieve erections by using another treatment which produces erections directly, without sexual stimulation. This treatment uses vasodilation (vessel dilation) by means of medications (vasodilators) which dilate the penile arteries so that the erectile chambers become engorged with blood to produce an erection. These medications relax the smooth muscle of penile arteries to cause arterial dilation.

The most common vasodilator is ALPROSTADIL® (Caverjet, Edex, Schwarz Pharma USA Holdings, Inc., Wilmington, Del.). It can be injected into the base of the penis (into one of the corpora cavernosa) with a needle or inserted into the urethra in pellet form through a delivery system called MUSE (Medicated Urethral Suppository for Erection). ALPROSTADIL® is effective in over 80% of patients and MUSE for about 30% of men with erectile dysfunction. For men for whom ALPROSTADIL® is ineffective, an injected mixture of vasodilators (TRIMIX) is effective for about 62% of patients.

Men who are able to achieve a normal erection but cannot sustain it because they have venous leakage may be helped by a penile constriction band. This is a ring-like device that is fastened around the base of the penis to keep blood from escaping. A penile band called Actis is available (Vivus Corp.).

A new medication Uprima (apomorphine), taken orally, is under study. It seeks to target mechanisms in the brain to produce an erection. It has been approved in Europe for treatment of erectile dysfunction.

A topical medication Topiglan (ALPROSTADIL®) has had promising results, applied to the head of the penis to produce an erection directly, without sexual stimulation. An ointment would ease the mode of delivery while reducing the risk of adverse effects compared to injection or urethral pellet.

Two oral medications, vardenafil and tadalafil, like sildenafil (VIAGRA®), are PDE-5 inhibitors which suppress the enzyme which breaks down the natural vasodilator cGMP in order to facilitate and maintain an erection.

When two or more medications are used in combination, the treatment is called combination pharmacotherapy. When a medication is used alone, the treatment is called monotherapy. When any monotherapy fails, a combination pharmacotherapy may be effective.

Combination pharmacotherapies using at least two medications have been used experimentally with significant results. The combination of VIAGRA® and MUSE has been evaluated (Eur. Urol. 2000; 38: 30-4 and BJU. Int. 2000; 86: 469-73 and Urol. 2000; 163: 198).

Another study evaluated the benefit of oral alpha blockers (daily oral doxazosin) in combination with intracavernosal (injected) ALPROSTADIL® (Urol. 1998; 52: 739-43).

Another study (Internat. J. Impot. Res. 2002; 14(1): 50-53) combined VIAGRA® with daily oral Cardura (doxazosin).

Angiotensin (Ang) peptides are a group of regulatory peptides in the renin-angiotensin system (RAS), which helps regulate blood pressure and extracellular volume in the body. Several angiotensin peptides are known, e.g., Ang-(2-8) (angiotensin III), Ang-(3-8) (angiotensin IV), Ang II (4-8), Ang II (5-8), Ang II (1-4), Ang-(1-9), and Ang-(1-7).

Ang-(1-7) is a biologically active heptapeptide of (RAS), and its functions are often opposite to those attributed to Ang II, which is the main effector component of RAS. Ang-(1-7) may be formed from Ang II via the angiotensin converting enzyme-2 (ACE-2), or directly from Ang I by action of neutral- or prolyl-endopeptidases. The receptor for Ang-(1-7) is the G-protein-coupled receptor Mas (see Santos R. A. S., et al. (2003). PNAS, USA, 100: 8258-8263). The major activities of Ang-(1-7) are vasodilation via stimulation of nitric oxide, prostaglandins and potentiation of bradykinin activities, and antidiuresis.

Other important activities of Ang-(1-7) are known, e.g., Ang-(1-7) may be involved in learning and memory mechanisms (see, Santos, R. A. and Campagnole-Santos, M. J. (1994) *Braz Med Biol Res.* 27(4):1033-47; Hellner, K., et al. (2005) *Mol Cell Neurosci.* 29(3):427-35).

Table 1 summarizes the biological activities of Ang-(1-7) and other important angiotensins (source: Ferreira A J, and Santos R A S. (2005). *Braz J Med Biol Res,* 38:499-507).

TABLE 1

Cardiovascular effects mediated by angiotensin receptors

| Angiotensin | Receptor | Actions |
| --- | --- | --- |
| Ang II | $AT_1$ | Vasoconstriction and pressor effect |
| | | Increase of inotropism and chronotropism |
| | | Arrhythmogenic effect |
| | | Remodeling and cell proliferation |
| | | Thrombosis and inflammation |

TABLE 1-continued

Cardiovascular effects mediated by angiotensin receptors

| Angiotensin | Receptor | Actions |
| --- | --- | --- |
| Ang II | $AT_2$ | Inhibition of cell proliferation |
| | | Apoptosis |
| | | Vasodilation |
| Ang-(1-7) | $AT_{1-7}$(Mas)* | Vasodilation |
| | | Potentiation of BK-induced vasodilation |
| | | Anti-arrhythmogenic effect |
| | | Improvement of post-ischemic contractile function |
| | | Inhibition of cell proliferation |
| Ang-(3-8) (Ang IV) | $AT_4$(IRAP) | Vasodilation |
| | | Inhibition of cell proliferation |
| Des-Asp1-Ang I | $AT_1$ | Inhibition of Ang II-induced cell proliferation |

*Mas-mediated actions are listed based on direct or indirect evidence (blocked by A-779).
Ang = angiotensin; BK = bradykinin; IRAP = insulin-regulated aminopeptidase The benefits of using Angiotensin-(1-7) in heart disease and its complications has been an important issue related to this heptapeptide. For example, U.S. Patent Application 2004/171584 discloses formulations comprising angiotensin-(1-7) and/or losartan for treatment of arterial hypertension and other cardiovascular diseases. In addition, U.S. Patent Application 2005/069533 discloses formulations of angiotensin-(1-7) for treating arterial hypertension, wounds, burns, erithema, tumors, alopecia, blood diseases, diabetes mellitus, sperm motility, nephropathy, gastrointestinal and gynaecological disorders, angiogenesis and angioplasty.

It is known that there are at least three different pathways to form Ang-(1-7) (see, e.g., Ferreira, A. J. and Santos, R. A. S. (2005) *Braz J Med Biol Res,* 38:499-507); Loot, A. E. (2005). Therapeutic perspectives of Angiotensin-(1-7) in heart failure. *Thesis Dissertation.* University of Groningen). Ang-(1-7) may be formed from Ang I (1-10), (i) directly, by combined action of neutral-endopeptidase and prolyl-endopeptidase (NEP and PEP), or (ii) indirectly, by hydrolysis of the intermediate Ang-(1-9) by action of angiotensin-converting enzyme and neutral-endopeptidase (ACE and NEP). Alternatively, Ang-(1-7) may be formed by hydrolysis of Ang II (1-8) by action of prolyl-carboxypeptidase, prolyl-endopeptidase and angiotensin-converting enzyme 2 (PCP, PEP and ACE2).

The sexual disturbances of the present invention are known to those skilled in the art (see, e.g., Diagnostic and Statistical Manual of Mental Disorders, Fourth Edition, (DSM-IV), American Psychiatric Association, Washington D.C., 1994 as well as the DSM-IV Guidebook, American Psychiatric Press, Inc., Washington D.C., 1995.

Thus, although impotence is a ubiquitous problem, there are few satisfactory methods available for treating this disorder. Therefore, it is an object herein to provide methods and compositions for treating impotence.

SUMMARY OF THE INVENTION

The present disclosure relates to the use of Ang-(1-7) in treating erectile dysfunction (ED). Ang-(1-7) can be used alone or in combination with other agents therapeutic for ED.

The disclosure also includes the use of Ang-(1-7) analogs in treating ED. Ang-(1-7) analogs can be used alone or in combination with other agents therapeutic for ED.

The disclosure also includes the use of Ang-(1-7) receptor agonists in treating ED. The Ang-(1-7) receptor agonists can be used alone or in combination with other agents therapeutic for ED.

A first embodiment of the instant invention refers to a pharmaceutical composition in an appropriate dosage form, said composition comprising: (a) Ang-(1-7) and/or an Angiotensin-(1-7) receptor agonist, and/or an Angiotensin-(1-7) analogue in an amount effective both to decrease erectile dysfunction symptoms and to restore erectile capacity; (b) optionally a PDE inhibitor, and (c) a pharmaceutically acceptable carrier. The pharmaceutical composition may further comprise an anti-hypertensive agent.

In a second embodiment, the present invention refers to a method for treating erectile dysfunction in an individual in needs of such a treatment, said method comprising administering to said individual an effective amount of Ang-(1-7) and/or an Ang-(1-7) receptor agonist, and/or an Ang-(1-7) analogue, alone or in combination with other active ingredients.

In a third embodiment, the present invention refers to a method for restoring erectile capacity in an individual in needs of such a treatment, said method comprising administering to said individual an effective amount of Ang-(1-7) and/or an Ang-(1-7) receptor agonist, and/or an Ang-(1-7) analogue, alone or in combination with other active ingredients, to restore erectile capacity.

In a preferred embodiment, the invention is an inclusion complex formed by Ang-(1-7) and a cyclodextrin.

Additional objects, features, and strengths of the invention will be made clear by the description below. Furthermore, the advantages of the present invention will be evident from the following explanation in reference to the drawings.

BRIEF DESCRIPTION OF THE DRAWINGS

The patent or application file contains at least one drawing executed in color. Copies of this patent or patent application publication with color drawing(s) will be provided by the Patent and Trademark Office upon request and payment of the necessary fee.

DETAILED DESCRIPTION OF THE INVENTION

Figure 1:
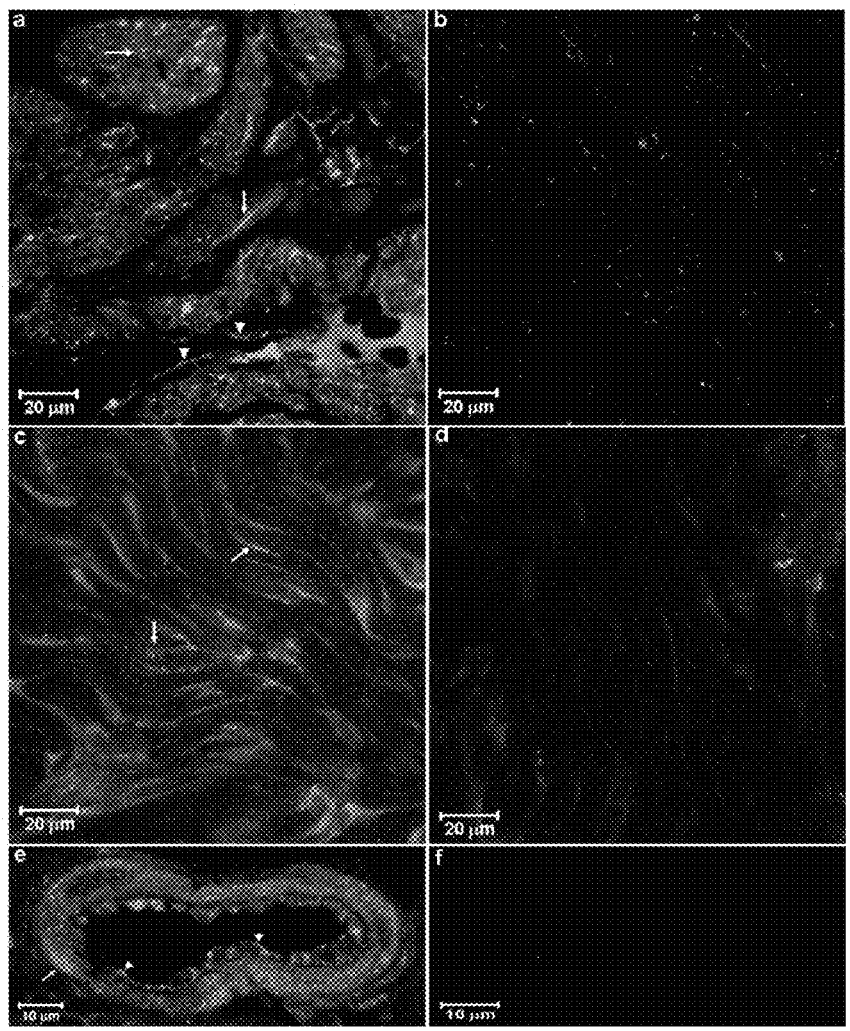
FIG. 1 shows the immunolocalization of Mas on human and rat penile structures. Mas was localized in human (a-b) and rat (c-d) cavernosal endothelial (triangles) and smooth muscle cell membranes (arrows), rat arteriolar endothelial and smooth muscle cells (d-e).

ED is a disorder involving the failure of a male mammal to achieve erection, ejaculation, or both. An increase in ED is often associated with age and is generally caused by a physical disease or as a side-effect of drug treatment. The major medications responsible for ED are anti-hypertensives (e.g., beta-blockers, sympathyolytics, and diuretics), and anti-diabetics.

ED and vascular disease (e.g., hypertension) are thought to be linked at the level of the endothelium. Endothelial dysfunction results in an inability of the smooth muscle cell lining in the arterioles to relax, thus preventing vasodilation.

Nitric oxide (NO) is a potent vasodilator and is secreted by the endothelium, being synthesized from L-arginine by the endothelial enzyme NO synthase (eNOS).

Ang-(1-7) promotes release of prostaglandins from vascular endothelial and smooth muscle cells, release of NO, vasodilation, inhibition of vascular cell growth and attenuation of Ang II-induced vasoconstriction.

The renin-angiotensin system has two major arms: a vasoconstrictor/proliferative arm in which the main mediator is Ang II acting on $AT_1$ receptors; and a vasodilator/anti-proliferative arm in which the major effector is Ang-(1-7) acting via the G protein-coupled receptor Mas. Renin-angiotensin system peptides, including the vasodilator Ang-(1-7), are widely released, including inside the corpus cavernosum (see, e.g., Kifor I., et al. (1997) *J Urol.* 157: 1920-1925).

The inventors demonstrate that Ang-(1-7) can be used to treat ED because: (i) the presence of the Mas in rat and human corpus cavernosum, (ii) the effect of Mas stimulation by Ang-(1-7) on NO release in human corpus cavernosum, (iii) the signaling mechanisms activated from NO release by Ang-(1-7); and (iv) activity in the in vivo models of penile erection.

Most causes of erectile dysfunction result from adverse effects on nerves or blood vessels to, from, or within the penis. Causes of erectile dysfunction include: atherosclerosis (thickening, narrowing, hardening and less elasticity of penile blood vessels); breakdown of chemical message to or within the penis (thereby preventing erectile chambers from becoming engorged with blood to produce erection); venous leakage (blood seeps out of the penile vessels); nerve and blood vessel damage caused by diabetes; nerve damage caused by degenerative diseases such as multiple sclerosis and Parkinson's disease; nerve damage caused by surgical removal of prostate, bladder or rectum; abdominal aortic aneurysm (penile nerves and vessels may be damaged); B-12 deficiency (causes neurological problems throughout the body); radiation treatments for prostate, bladder or rectal cancer; psychological factors (stress, depression, performance anxiety); hormonal imbalances such as testosterone deficiency or abnormally high levels of prolactin; alcohol; tobacco usage; substance abuse; Peyronie's disease (penile connective tissue thickens thereby interfering with the ability to have an erection); injury to nerves or arteries necessary to have an erection (pelvic fracture, brain, spinal cord, abdomen or penis); anti-hypertensives; anti-depressants; tranquilizers; anti-fungals; antacids; cholesterol-lowering drugs; diuretics; nitrates; Proscar (medication for benign prostate hyperplasia); propecia (to counteract baldness); estrogens; anti-androgens; anti-histimines; anti-cholinergics; anti-cancer drugs; aging, hypertension; obesity; and hyper-cholesterolemia.

The present disclosure particularly relates to the use of Ang-(1-7) and/or Ang-(1-7) receptor agonist and/or Ang-(1-7) analogue in treating erectile dysfunction (ED) in a patient in need thereof, wherein the erectile dysfunction is caused by diabetes, kidney disease, chronic alcoholism, multiple sclerosis, atherosclerosis, vascular disease, neurological disease or psychological disease. Ang-(1-7) and/or Ang-(1-7) receptor agonist and/or Ang-(1-7) analogue can be used alone or in combination with other active ingredient.

Further, the present invention is particularly related to the use of Ang-(1-7) and/or Ang-(1-7) receptor agonist and/or Ang-(1-7) analogue in treating/restoring erectile dysfunction (ED) in a patient in need thereof, wherein the erectile dysfunction is caused by anti-hypertensives, anti-histamines, anti-depressants, tranquilizers, appetite suppressants, or by surgery or injury that affects penile erection.

The present invention also provides a pharmaceutical composition in an appropriate dosage form, said composition comprising a PDE-inhibitor combined with Ang-(1-7) and/or Ang-(1-7) receptor agonist and/or Ang-(1-7) analogue and a pharmaceutical carrier. The composition may further comprise an anti-hypertensive agent.

The term "Angiotensin-(1-7)" as used herein, is the heptapeptide having the sequence Asp-Arg-Val-Tyr-Ile-His-Pro. The terms "Angiotensin-(1-7) receptor agonist" and "Angiotensin-(1-7) analog" are intended to include peptidic agonists or analogues, and non-peptidic agonists, e.g., $Ala^1$-Angiotensine-(1-7), AVE 0991 and those disclosed in U.S. Patent Application 2005/069533. which is herein incorporated by reference in its entirety. Also included are nonpeptidic agonists e.g., in U.S. Pat. No. 6,235,766 which is hereby incorporated by reference in its entirety.

The term "anti-diabetic agent" as used herein, is intended to include, but is not limited to, insulin secretion enhancers, e.g., a biguanide derivative, for example, metformin or a pharmaceutically acceptable salt thereof. Other insulin secretion enhancers include sulfonylureas (SU), including tolbutamide; chlorpropamide; tolazamide; acetohexamide; 4-chloro-N-[(1-pyrrolidinylamino)carbonyl]-benzensulfonamide (glycopyramide); glibenclamide (glyburide); gliclazide; 1-butyl-3-metanilylurea; carbutamide; glibonuride; glipizide; gliquidone; glisoxepid; glybuthiazole; glibuzole; glyhexamide; glymidine; glypinamide; phenbutamide; and tolylcyclamide, or pharmaceutically acceptable salts thereof.

The term "anti-hypertensive agent" as used herein, is intended to include, but not being limited to, Angiotensin II receptor antagonists, e.g. losartan, candersartan, irbersartan, valsartan, olmesartan, eprosartan, telmisartan; β-blocker agents; calcium channel blocker agents; ACE-inhibitors, e.g. captopril, enalapril, fosinopril, delapril, benzepril; and diuretic agents.

The term "β-blocker agent" as used herein, is intended to include but not being limited to, acebutolol, atenolol, betaxolol, bisoprolol, esmolol, metropolol, propanolol, timolol, pindolol, penbutolol, labetalol, carvedilol. Atenolol was used as an example of β-blocker agent used in the composition of the invention.

The term "diuretic agent" as used herein, is intended to include but not being limited to, chlorothiazide, chlorthalidone, furosemide, hydrochlorothiazide, mannitol, metolazone, amiloride and hydrochlorothiazide mix, triamterene and hydrochlorothiazide mix, and potassium-sparring diuretics, such as amiloride, spironolactone, and triamterene.

The term "PDE inhibitors" as used herein, is intended to include, but not being limited to, nonselective phosphodiesterase inhibitors, e.g. papaverine, and phosphodiesterase 5 inhibitors, such as sildenafil, vardenafil and tadalafil or a pharmaceutically acceptable salt thereof.

An "effective amount" is one that is sufficient to achieve improvement in erectile function or an alleviation of the symptoms of erectile dysfunction, or even to restore the erectile capacity. Effective amounts will depend on the specific condition being treated and the severity thereof; individual patient characteristics, including age, physical condition, size and weight; concurrent treatment; and the mode of administration. These factors are well known to those skilled in the art and can be established without under experimentation. Generally, doses of Ang-(1-7) or Ang-(1-7) receptor agonist or Ang-(1-7) analogue will range from about 0.01 μg/kg body weight per day to 100 μg/kg body weight per day, preferably from 0.1 μg/kg body weight per day to 10 μg/kg body weight per day. Multiple doses per day, in most cases, may be contemplated to achieve appropriate systemic levels of active ingredients present in the composition of the invention.

Ang-(1-7), Ang-(1-7) receptor agonists, or Ang-(1-7) analogues described herein may be those commercially available, or are derived from commercially available compounds, or are synthesized de novo by using no more than routine procedures which are known to skilled persons in the art of peptide preparation.

The compositions of the present invention may be administered by a variety of administration routes, including, but not being limited to, oral, intracavernosal injection, topically and transdermally delivered through the skin into various sites or parenteral routes. The particular mode selected will depend on the active ingredients present in the composition, the severity of the erectile dysfunction being treated and the dosage required for therapeutic efficacy. Preferably, the compositions of the invention are in oral administration form because of convenience of the patient and the dosing schedule.

In one embodiment, the present invention relates to a method for treating ED by administering to an individual in needs of such a treatment an amount of Ang-(1-7) effective to decrease the symptoms of ED. The Ang-(1-7) can be administered in an effective dose which maintains systemic blood pressure in levels higher than those that can cause sexual dysfunction. Preferably, the therapeutically effective dose is sufficient to maintain intracavernosal pressure to a level substantially close to the mean arterial pressure.

In another embodiment, the present invention relates to a method for restoring erectile capacity by administering to a patient an amount of Ang-(1-7) and/or Ang-(1-7) receptor agonist and/or Ang-(1-7) analogue, either alone or combined with other active ingredients effective to restore the erectile capacity.

The compositions containing Ang-(1-7) may be prepared by any of the methods well known in the state of the art. Appropriately, teachings of Remington's Pharmaceutical Sciences or of a similar information source may be used to prepare a suitable formulation according to the invention.

Where injectable compositions are selected, the formulation for parenteral administration preferably comprises a sterile aqueous preparation of Ang-(1-7) and other active ingredients. The sterile injectable preparation may be appropriately a sterile injectable solution or suspension in a non-toxic parenterally-acceptable diluent or solvent which are known to the skilled person in the art of pharmacy.

According to the invention, compositions for oral administration may be presented as discrete units such as capsules, tablets, effervescent tablets, chewable tablets, pills, powders, granules and gels or similar pharmaceutical forms. Other oral formulation forms include suspensions or emulsions in an aqueous or non-aqueous carrier.

In the solid dosage forms, the active ingredients can be admixed with a pharmaceutically acceptable carrier comprising at least one component selected from the group comprising diluents, binders, disintegrants, lubricants, coloring agents, and flavoring agents. Exemplary inert diluents are calcium carbonate, calcium phosphate-dibasic, calcium phosphate-tribasic, calcium sulfate, cellulose-microcrystalline, cellulose powdered, dextrates, dextrins, cyclodextrins, dextrose excipients, fructose, kaolin, lactitol, lactose, mannitol, sorbitol, starch, starch pregelatinized, sucrose, sugar compressible, and sugar confectioners. As binders may be used one or more substances, e.g., methyl cellulose, hydroxypropyl cellulose, hydroxypropyl methyl cellulose, polyvinylpyrrolidone, gelatin, gum arabic, ethyl cellulose, polyvinyl alcohol, pullulan, pregelatinized starch, agar, tragacanth, sodium alginate, propylene glycol, and alginate. As desintegrant may be used one or more substances selected from low substituted hydroxypropyl cellulose, carboxymethyl cellulose, calcium carboxymethyl cellulose, sodium carboxymethyl cellulose, croscarmellose sodium, starch, crystalline cellulose, hydroxypropyl starch, and partially pregelatinized starch, and croscarmellose sodium. Exemplary lubricants are stearic acid, magnesium stearate, calcium stearate, talc, hydrogenated castor oil, sucrose.

According to the invention, in the case of capsules, tablets, effervescent tablets, and pills, the dosage forms can also comprise buffering agents. Soft gelatin capsules can be prepared to contain a mixture of the active ingredients of the invention and vegetable oil. Hard gelatin capsules may contain granules of the active ingredients in combination with a solid, pulverulent carrier such as, lactose, saccharose, sorbitol, mannitol, potato starch, corn starch, amylopectin, cellulose derivatives of gelatin. In addition, tablets and pills can be prepared with enteric coatings.

Particularly preferred according to the present invention are dosage forms of a controlled/retarded/modulated release type, which are based on carriers or matrices including, but not being limited to, biocompatible polymers, pharmaceutically acceptable polymeric matrices, liposomes, PEG-liposomes, or a cyclodextrin or a cyclodextrin derivative matrix. Especially preferred are dosage forms comprising active ingredients encapsulated in a cyclodextrin matrix as disclosed in U.S. Patent Application 2005/069533 which is herein incorporated as reference in its entirety. In such an embodiment, the cyclodextrin is selected from the group consisting of alkylated cyclodextrin, hydroxyalkylated cyclodextrin, and acylated cyclodextrin. Particularly preferred is a hydroxyalkylated cyclodextrin, and more preferred is the hydroxypropyl β-cyclodextrin. Further, cyclodextrin derivatives are described in Szejtli, J. Chem Rev, (1998), 98, 1743-1753; and Szente, L and Szejtli, J., Advance Drug Delivery Reviews, 36 (1999) 17-28, which are hereby incorporated by reference in their entirety. Examples of cyclodextin derivatives include methylated CDs (RAMEB=randomly methylated β-cyclodextrin); hydroxyalkylated CDs (hydroxypropyl-β-CD and hydroxypropyl γ-cyclodextrin); acetylated CDs (acetyl-γ-cyclodextrin); reactive CDs (chlorotriazinyl β-CD); and branched CDs (glucosyl- and maltosyl β-CD); acetyl-γ-cyclodextrin; acetyl-β-CD, sulfobutyl-β-CD, sulfated α-, β- and γ-cyclodextrins; sulfoalkylated cyclodextrins.

In the most preferred embodiment, the composition of the invention comprises a hydroxypropyl β-cyclodextrin-Ang-(1-7) (Ang-(1-7)/HPβ-CD) Inclusion Complex.

The following will describe the present invention in more detail by way of Examples. It should be noted that the invention is not limited by the following description.

EXPERIMENTAL

Animals

Intact male Wistar rats (220-250 g), Swiss male mice, Mas-KO (Mas$^{-/-}$) male mice on the pure genetic background C57BL/6, and WT C57BL/6 control mice (Mas+/+) bred at the animal facility of the Biological Science Institute (CEBIO, Federal University of Minas Gerais, Minas Gerais, Brazil) were used in the assays for practicing the instant invention. Animals were kept in temperature-controlled rooms, with 14/10 h light/dark cycle (lights at 6:00 am) with free access to water and food. The animal care committee from the Federal University of Minas Gerais, Brazil, approved all experimental protocols.

Surgical Procedure

Normotensive and DOCA-salt hypertensive rats, Mas−/− and WT mice were anesthetized with intraperitoneal urethane (140 mg/Kg). The rat left femoral artery and mice coronary artery was cannulated for continuous monitoring of mean arterial pressure (MAP). The shaft of the penis was freed of skin and fascia, and the right corpus cavernosum was cannulated by insertion of a 30-gauge needle connected to a pressure transducer, permitting continuous monitoring of corpus cavernosum pressure (CCP) as described elsewhere (see, e.g., T. M. Mills, et al., *Biol Reprod* 59, 1413 (December, 1998)). The rat left corpus cavernosum was cannulated with 30-gauge needles attached to 10-μL syringes via short lengths of polyethylene (PE)-10 tubing and used for administration of vasoactive drugs. The abdominal cavity was opened, exposing the right major pelvic ganglion (MPG), and silver bipolar electrodes were positioned on it.

Animal Model

Male Wistar rats (130-150 g) were uninephrectomized and impregnated with a subcutaneous silastic implant containing DOCA (200 mg/kg) under tribromoethanol anesthesia (e.g., F. Ammarguellat, et al. *Circulation* 103, 319 (Jan. 16, 2001)). Animals were maintained on water containing 1.0% NaCl and 0.2% KCl for 4 weeks. Sham animals were uninephrectomized but did not receive a DOCA implant and were maintained on normal drinking water. Systolic blood pressures were measured using standard tail-cuff procedures.

Human Tissue

Discarded fragments of human corpus cavernosum (HCC) tissue were retrieved during implant of penile prostheses or prostate cancer surgery, and were placed in ice-cold Krebs solution for rapid transport to the laboratory. HCC strips from patients with (H-ED) and without erectile dysfunction (H-WED) were studied.

Immunohistochemistry Procedure

The animals were killed and corpus cavernosum was withdrawn. Strips of rat corpus cavernosum and HCC were placed in 4% paraformaldehyde for 2 h. Subsequently, adjacent tissue sections (10 μm) were made in a cryostat. After this period, the sections were incubated in PBS, tween 0.2%, and BSA 5%, each one for 15 min, and then sequentially incubated with primary antibody (1:500) or control solution [consisting of primary antibody (1:500) pre-incubated for 24 hours at 4° C. with 50 μg of blocking peptide corresponding to the N-terminus of the Mas protein], for 24 h, at 4° C. After primary antibody or control solution incubation, the sections were washed in PBS (3 times for 5 min), and subsequently incubated with the secondary antibody (1:400, Alexa 594, Molecular Probes) for 2 h at ambient temperature. The reaction was stopped in Tris buffer (50 mM) and tissues were mounted on chrome-alum coated slides, air dried, and coverslipped with glycerol/Tris mounting media. Fluorescent images were obtained using a Zeiss 510 meta laser scanning confocal microscope equipped with an oil-immersion objective lens (×63).

DAF NO Measurement

Human and mouse corpus cavernosum were loaded with DAF-FM (1.0 μM) or DAF-FM plus Ang-(1-7) (1.0 μM and 10.0 nM, respectively) during 10 minutes at ambient temperature. Subsequently, the strips were washed in PBS (3 times for 5 min) and frozen overnight at −80° C.

Rats were anesthetized with intraperitoneal urethane (140 mg/Kg). The shaft of the penis was freed of skin and fascia, and the right corpus cavernosum was cannulated by insertion of a 30-gauge needle attached to 10-μL syringes via short lengths of PE-10 tubing used for infusion of DAF (1.0 μM) or DAF plus Ang-(1-7) solutions (1.0 μM and 15.5 pmol/Kg/min, respectively—0.5 μL/min during 5 min.). In some preparations, the abdominal cavity was opened, exposing the right major pelvic ganglion, and silver bipolar electrodes were positioned on it. A submaximal stimulus was applied during 2 minutes while solution was infused into cavernosal sinuses as described above. The animals were killed and corpus cavernosum was withdrawn and frozen at −80° C.

Adjacent tissue sections (20 μm) were prepared using a cryostat. Tissues were mounted upon chrome-alum coated slides, air dried, and coverslipped with glycerol/Tris mounting media. Fluorescent images were obtained using a laser scanning confocal microscope excited at 488 nm with argon-ion laser (oil-immersion objective lens ×63).

Cells

Chinese hamster ovary (CHO) cells were stably transfected with rat Mas cDNA driven by a cytomegalovirus promoter and selected by neomycin as previously described (J. B. Pesquero et al., *J Biol Chem* 269, 26920 (Oct. 28, 1994)). The cells were cultured at 37° C. in DEMEM/F12 (GIBCO™), supplemented with 10% fetal bovine serum in a water-saturated atmosphere of 95% $O_2$ and 5% $CO_2$.

Western Blotting

Cells were rendered quiescent in serum-free medium 12 h before stimulation. Cells were exposed to Ang-(1-7), ($10^{-7}$M, 5 to 30 min) in the presence or absence of its inhibitor, A-779 ($10^{-6}$ M, 10 min preincubation). Whole cells lysates were prepared and western blotting was performed as described (R. M. Touyz et al., *Circ Res* 90, 1205 (Jun. 14, 2002)). Briefly, protein concentrations of the cell lysates were determined, the lysates were subjected to electrophoresis on 7.5% sodium dodecyl sulfate-polyacrylamide gels (SDS-PAGE) and transferred to a nitrocellulose membrane. Blots were blocked with 5% skimmed milk and incubated with specific antibodies. Phosphorylation of eNOS(S1177) was measured using a phospho-specific antibody (51177, 1:1000, Cell Signaling Technology, Beverly, Mass.). $AT_1$, $AT_2$ and Mas receptor expression were detected using specific antibodies (AT1, 1:500, Santa Cruz Biotechnology, $AT_2$ 1:500, Alpha Diagnostics, San Antonio, Tex.; Mas, 1:1000). β-actin antibody (1:1000, Santa Cruz Biotechnology) was used to confirm the equal loading. Immunoreactive proteins were detected by chemiluminescence, and blots were analyzed densitometrically (Image-Quant software, Molecular Dynamics).

NO Release

CHO cells, cultured in 6 well-dishes were stimulated in a dose-dependent manner with Ang-(1-7) ($10^{-8}$ to $10^{-6}$ M). The nitrite amount over 30 min was measured using the fluorochrome 2,3-diaminonaphthalene (DAN) method as previously described (D. J. Kleinhenz, X. Fan, J. Rubin, C. M. Hart, *Free Radic Biol Med* 34, 856 (Apr. 1, 2003)).

Histology

Histological technique was applied to the $Mas^{+/+}$ and $Mas^{-/-}$ mice corpus cavernosum. In the first instance, fresh tissue specimens were frozen at −80° C. Sections of 20 microns were cut from the fresh tissue specimens and subjected to histological technique, specifically, Gomori trichromes. Microscopic data were digitally captured.

For quantitative analysis of fibrous tissue content the intensity of staining in different areas of the corpus cavernosum from Mas+/+ and Mas−/− is measured. Image of these areas were captured at 12 bits using a gray scale range of 0 to 255. These areas were compared and analyzed using the Scion Image software (www.scioncorp.com).

Statistical Analysis

All results are expressed as mean±s.e.m. Statistical analysis was performed by two-way ANOVA followed by Bonferroni pos-test. To analyze the intracavernosal effect of the A-779 and influence of L-NAME on Ang-(1-7) effect, unpaired Student t test was used. Statistical analysis of fibrous tissue content was performed using unpaired Student t test followed by the Mann Whitney test. A p value <0.05 was considered significant.

Effect of Ang-(1-7) on Ganglionic-Stimulated Changes in CCP/MAP

To examine the effect of Ang-(1-7) on ganglionic-stimulated changes in CCP/MAP, the nerve was stimulated with range of voltages (0.5, 0.75, 1.0, 1.2, 1.5, 2.0, 2.5 and 3.0 V, 5 msec pulses at a frequency of 12 Hz), following intracavernosal infusion of Ang-(1-7) (at a dose of the 15.5 pmol/Kg/min, 0.5 µL/min). Subsequently, ganglionic stimulation was repeated.

To examine the effect of Mas antagonism on Ang-(1-7) ganglionic-induced CCP/MAP rise, after initial measurements of CCP and MAP, A-779 and Ang-(1-7) were simultaneously administered, and ganglionic stimulation was repeated.

In order to evaluate the role of the Ang-(1-7) released endogenously, it was first determined the minimal stimuli in which the maximal value of the CCP/MAP was achieved. Subsequently (10 minutes later), A-779 (155 pmol/Kg/min) was infused into cavernosal sinuses and the stimulation was repeated.

To evaluate the effect of Ang-(1-7) on ganglionic-stimulated CCP/MAP rise in the presence of NOS inhibition, a sub-maximal stimulus was determined and applied to the MPG. Subsequently, L-NAME (200 µg/Kg) was intracavernously injected and ganglionic stimulation was repeated. Thereafter, Ang-(1-7) was administered and sub-maximal stimulus was applied while CCP/MAP was continuously recorded.

Example 1

Determining Immunolocalization of Mas on Human and Rat Penile Structures

Using immunofluorescence, at first the Ang-(1-7) receptor Mas was localized in rat and human penile structures. Human and rat corpus cavernosum slices were incubated for 24 hours with a polyclonal anti-Mas mouse primary antibody or control solution [primary antibody (1:500) pre-incubated for 24 hours at 4° C. with 50 µg of blocking peptide corresponding to the N-terminus of the rat Mas protein, and subsequently, with Alexa 594-labeled goat anti-mouse IgG for 2 hours. FIG. 1 shows that Mas is localized in the human and rat cavernosal smooth muscle cell membrane, rat spongisum smooth muscle and arteriolar endothelial cells.

Figure 2:
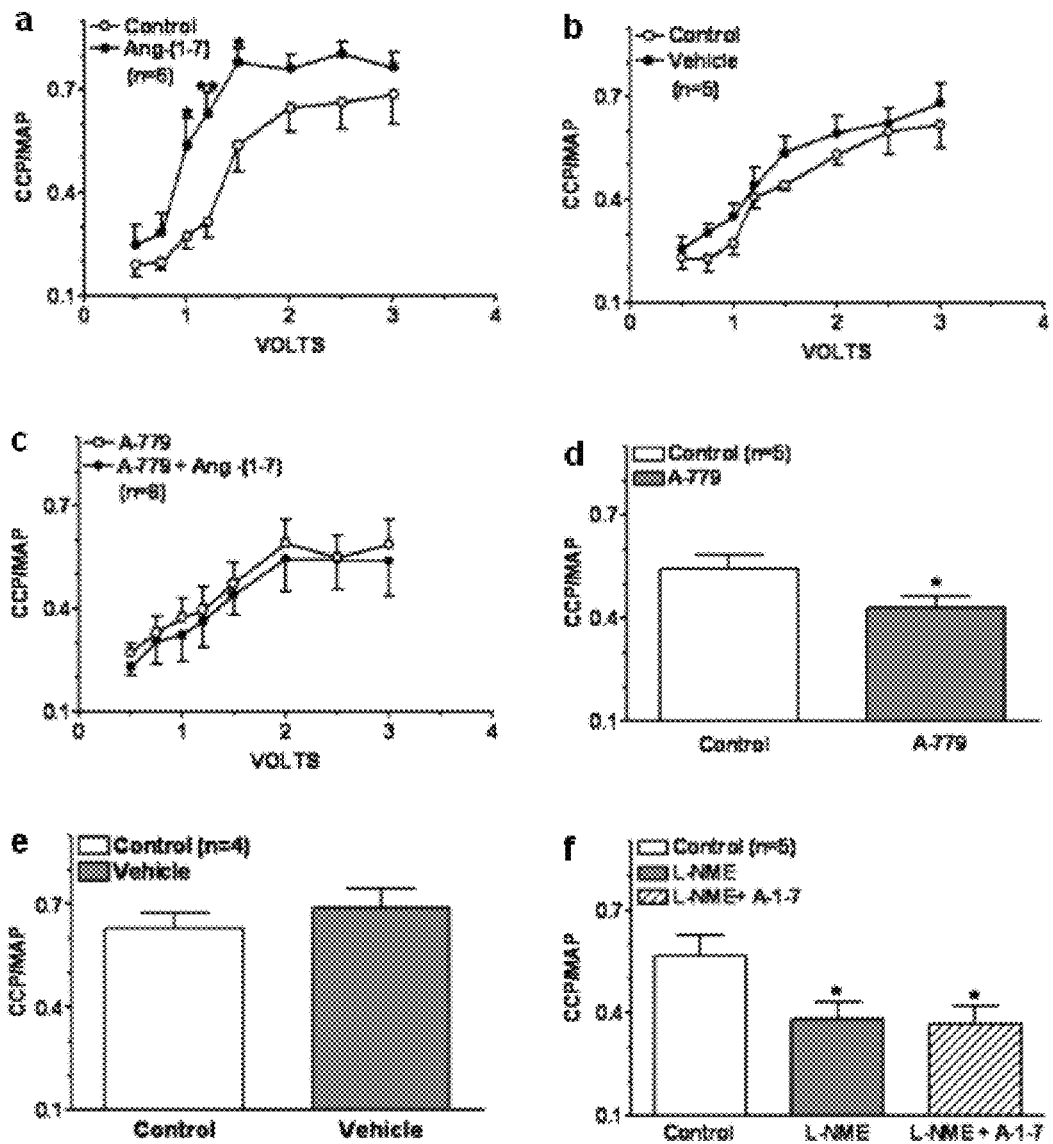
FIG. 2 graphically illustrates the in vivo effect of Ang-(1-7) on rat ganglionic-stimulated erectile response. Ang-(1-7) (a-b) increased the CCP/MAP rise induced by ganglionic stimulation that was blunted by A-779 infusion (c). A-779 reduces CCP/MAP rise induced by minimal stimuli in which the maximal value of the CCP/MAP was observed (d-e). L-NAME attenuated CCP/MAP rise induced by electrical stimulation that was not overcome by Ang(1-7) (f). All results are expressed as mean±s.e.m. Statistical analysis was performed with ANOVA followed by Bonferroni post hoc test. *, P<0.05, ** P<0.01 compared with control, recorded 10 min before drug administration. t Test was performed in the A-779 and L-NAME protocol. * P<0.05 compared with control.

Using an in vivo rat model, the next step was to examine the effect of intracavernosal infusion of Ang-(1-7) on corpus cavernosum pressure (CCP) and mean arterial pressure (MAP). Electrical stimulation of the major pelvic ganglion (MPG) resulted in a voltage-dependent increase in the CCP/MAP ratio, consistent with previous studies on penile erection mechanisms (e.g., K. K. Chen, et al., *J Urol* 147, 1124 (April, 1992); K. Chitaley, et al., *Int J Impot Res* 13 Suppl 5, S16 (December, 2001); and C. M. Reilly, et al. *J Androl* 18, 110 (March-April, 1997). As illustrated in FIG. 2 *a-b*, injection of Ang-(1-7) produced a small but significant increase in CCP without altering baseline MAP (CCP/MAP mean±SEM→Before: 0.17±0.014, n=10; After Ang-(1-7): 0.25±0.027; P<0.05, n=10). Strikingly, Ang-(1-7) markedly potentiated the increase of the CCP/MAP ratio induced by ganglionic stimulation. This effect was abolished by the receptor Mas antagonist A-779 (see FIG. 2*c*), as previously described (see R. A. Santos et al., *Brain Res Bull* 35, 293 (1994)). Of note, as illustrated in FIG. 2*d-e*, intracavernosal infusion of A-779 attenuated CCP/MAP increase induced by the minimal stimulation in which the maximal value of the CCP/MAP was achieved, suggesting that Ang-(1-7) released endogenously contribute for the ganglionic stimulated CCP/MAP rise.

Example 2

The Potentiating Effect on Erectile Function Produced by Ang-(1-7) is NO Dependent To determine whether the potentiating effect on erectile function produced by Ang-(1-7) was NO dependent, additional experiments in the presence of the NOS inhibitor, $N_w$-nitro-$_L$-arginine methyl ester (L-NAME) was performed. Administration of L-NAME into the left cavernosal sinuses did not alter baseline CCP or MAP. On the other hand, as expected (see previous descriptions in C. M. Reilly et al. (1997), and K. Chitaley et al., *Nat Med* 7, 119 (January, 2001)), L-NAME treatment significantly attenuated the increase in CCP/MAP induced by submaximal stimulus [mean±s.e.m. Contr.: 0.57±0.06 versus L-NAME: 0.38±0.05; P<0.05, n=6]. The attenuated erectile response induced by NOS inhibition was not overcame by administration of Ang-(1-7), suggesting that NO is an important downstream mediator of its potentiating effect in this experimental model. This result is illustrated in FIG. 2*f*.

Example 3

Ang-(1-7) Releases NO in the Corpus Cavernosum

Figure 3:
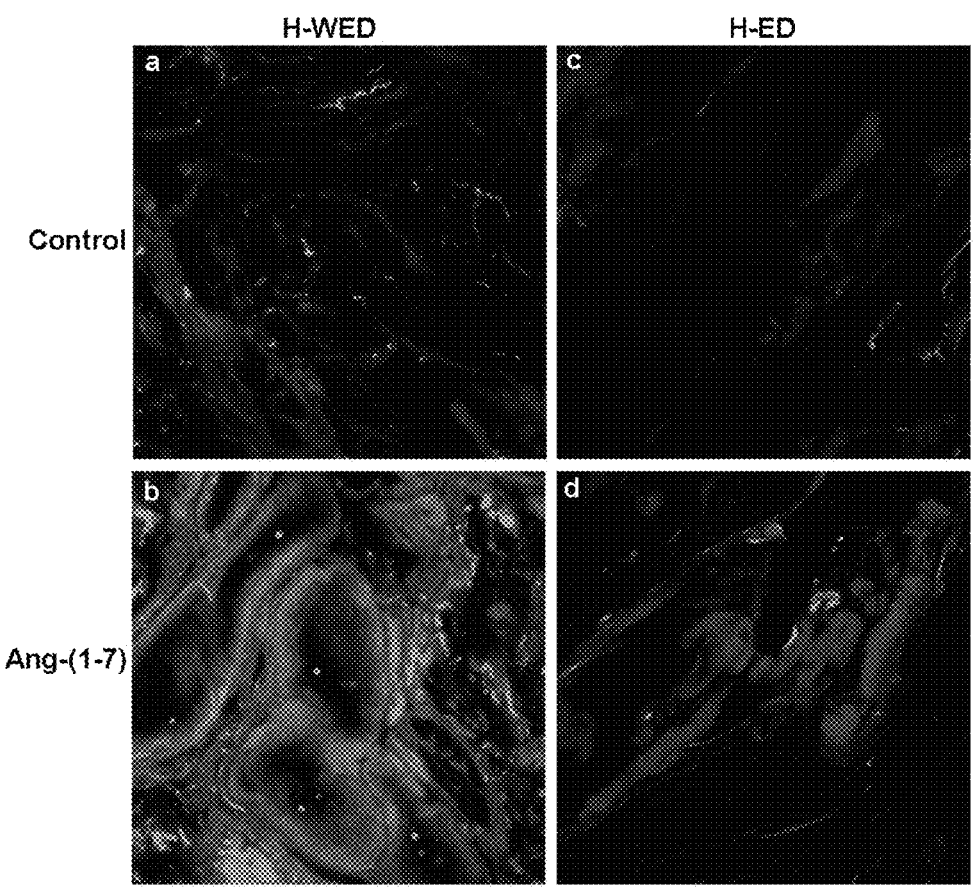
FIG. 3 shows nitric oxide released in human corpus cavernosum induced by Ang-(1-7). Ang-(1-7) stimulated NO release into cavernosal tissue from humans without (a-b) and with (c-d) erectile dysfunction. H-WED, human without erectile dysfunction; H-ED, human with erectile dysfunction.
Figure 4:
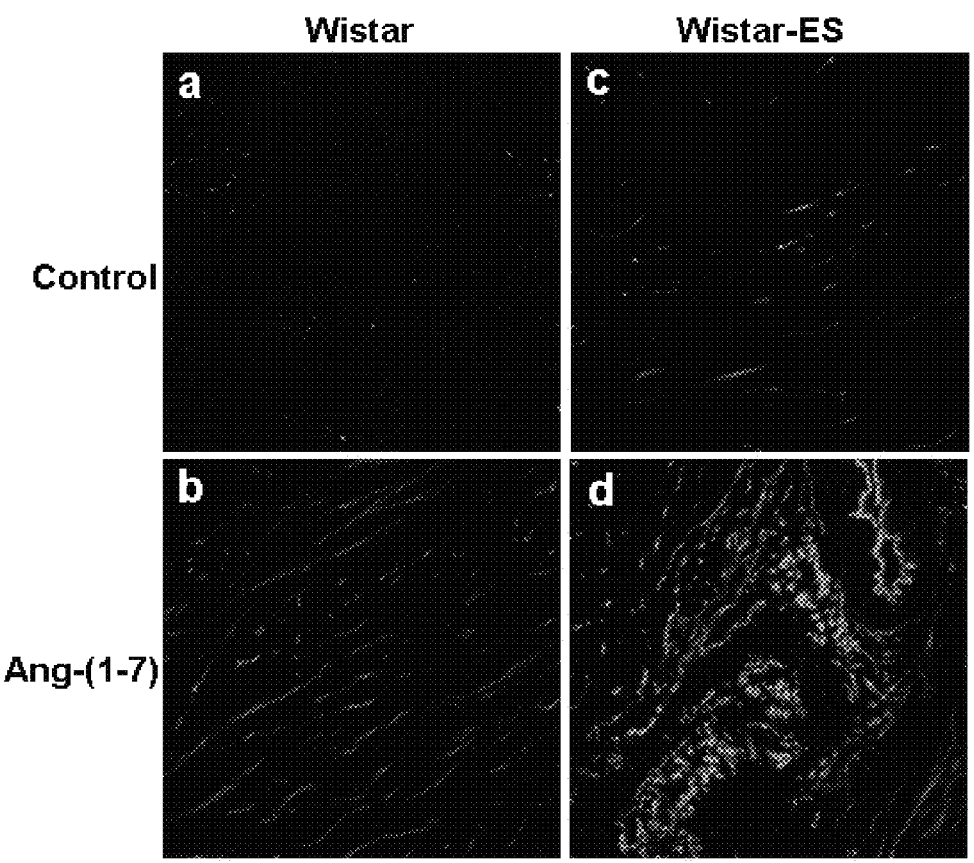
FIG. 4 illustrates nitric oxide released in rat corpus cavernosum induced by Ang-(1-7). Ang-(1-7) induced NO release in non-stimulated rat corpus cavernosum (a-b). Submaximal ganglionic stimulation of rat induced NO release, which was increased by Ang-(1-7) (c-d). ES, electrically stimulated.
Figure 5:
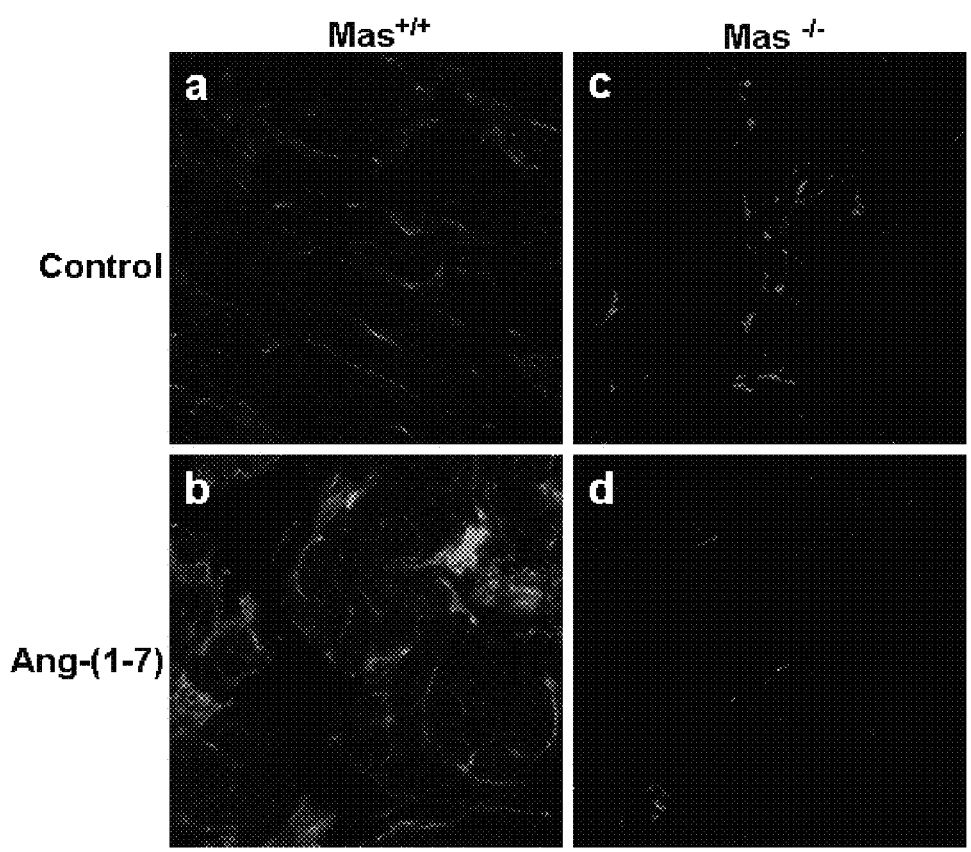
FIG. 5 shows nitric oxide released in mice corpus cavernosum induced by Ang-(1-7). Ang-(1-7) stimulated NO release in Mas WT mice (a-b) that was abolished in Mas-knockout mice (c-d). WT, wide type mice; KO, knockout mice.

To further demonstrate that Ang-(1-7) releases NO in the corpus cavernosum, the NO indicator 4-amino-5 methylamino-2',7'-difluorofluorescein diacetate (DAF-FM) was used (see A. Patzak et al., *Kidney Int* 66, 1949 (November, 2004)). Corpus cavernosum strips of human, Mas-deficient mice (see T. Walther et al., *J Biol Chem* 273, 11867 (May 8, 1998)) and Mas wild type (WT) animals were loaded with DAF-FM or DAF-FM combined with Ang-(1-7) solution. In the in vivo rat protocol, the same solutions were infused into cavernosal sinuses during 5 min with or without electrical stimulation. In human with (H-ED) and without (H-WED) erectile dysfunction (see FIG. 3 *a-d*), rat (see FIG. 4 *a-b*) and WT mice corpus cavernosum (see FIG. 5 *a-b*), Ang-(1-7) induced a substantial NO release into corpus cavernosum. As illustrated in FIG. 4 *c-d*, electrical stimulation of MPG with submaximal stimulus induced NO release into rat corpus cavernosum that was markedly potentiated by Ang-(1-7). NO release induced by Ang-(1-7) was absent in Mas-knockout mice as shown on FIG. 5 *c-d*.

Example 4

NO Accumulation Induced by Ang-(1-7) is Due to Direct Effect on NO Production

Figure 6:
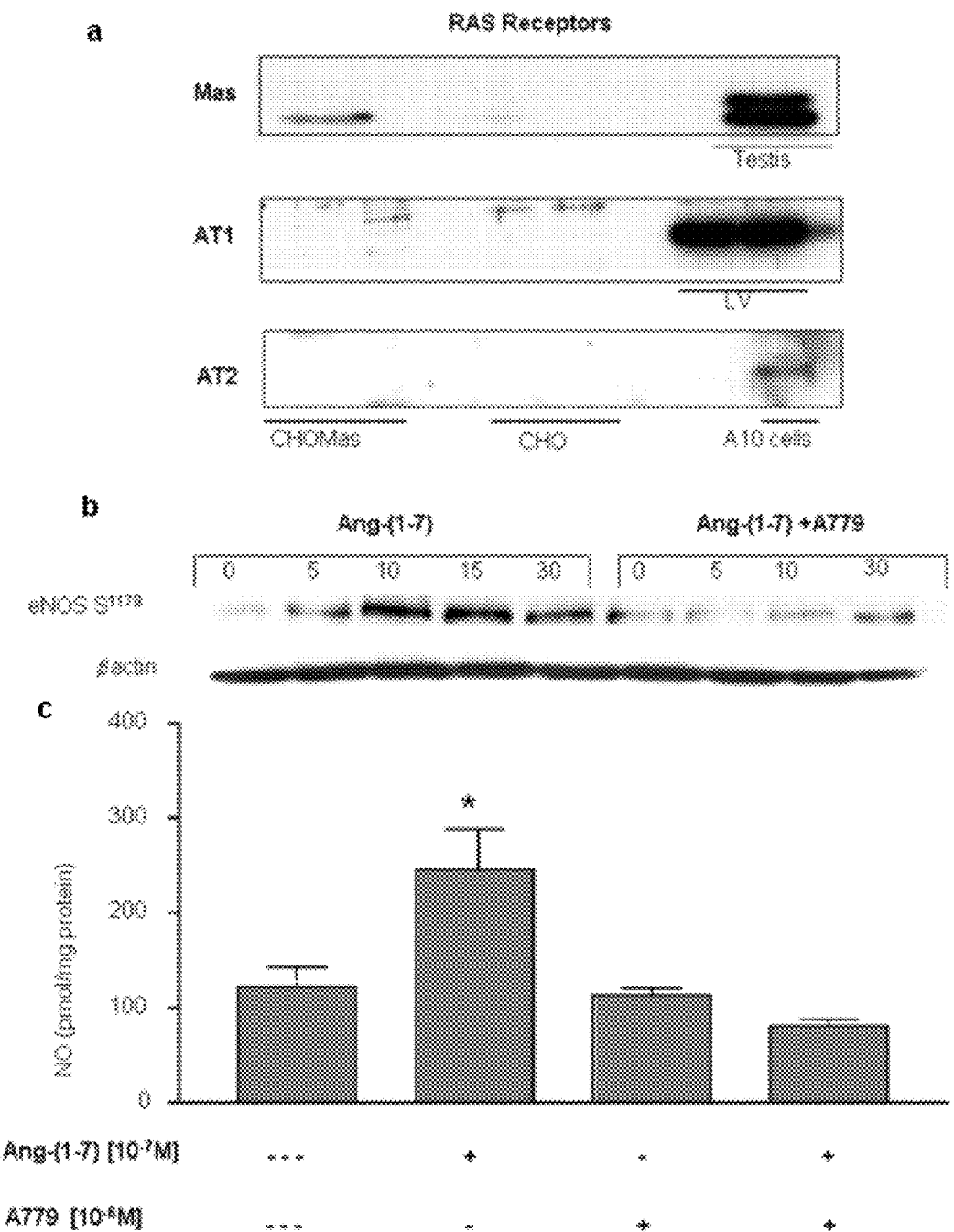
FIG. 6 illustrates blots showing that Ang-(1-7) stimulates the phosphorylation of eNOS (S1177) and increases eNOS activity in CHO-Mas transfected cells. a, Mas $AT_1$ and $AT_2$ receptor expression in CHO and CHO-Mas transfected cells detected by western blotting analysis with specific antibodies. b, Time-dependent increase in eNOS phosphorylation. CHO-Mas transfected cells were exposed to Ang-(1-7), ($10^{-7}$M, 5 to 30 min) in the presence or absence of its inhibitor, A-779 ($10^{-6}$ M) and eNOS phosphorylation detected by western blotting analysis with phospho-specific antibody (S1177). Phosphorylation was completely blocked by the Ang-(1-7) antagonist, A-779. c, Ang-(1-7) induced NO release in a dose-dependent manner. NO release over 30 min was measured using the fluorochrome 2,3-diaminonaphthalene (DAN). * P<0.05 (LV, left ventricle).

To test whether the NO accumulation induced by Ang-(1-7) was due to direct effect on NO production, a determination of the effect of the heptapeptide on the endothelial NOS phosphorylation was accomplished. For these experiments, Mas-transfected CHO cells (CHO-Mas) were used to avoid the interference of other receptors. As shown in FIG. 6*a*, these cells do not express $AT_1$ or $AT_2$ receptors. Ang-(1-7) phosphorylates eNOS at serine 1179, which was blocked by A-779

(see FIG. 6b). To confirm the viability of the CHO-Mas, these cells were incubated with Ang-(1-7), or A-779, or Ang-(1-7) plus A-779. As observed in FIG. 6c, Ang-(1-7) increased NO release by CHO-Mas, and this effect was blocked by A-779.

Example 5

Effects of Ang-(1-7) on ED

Figure 7:
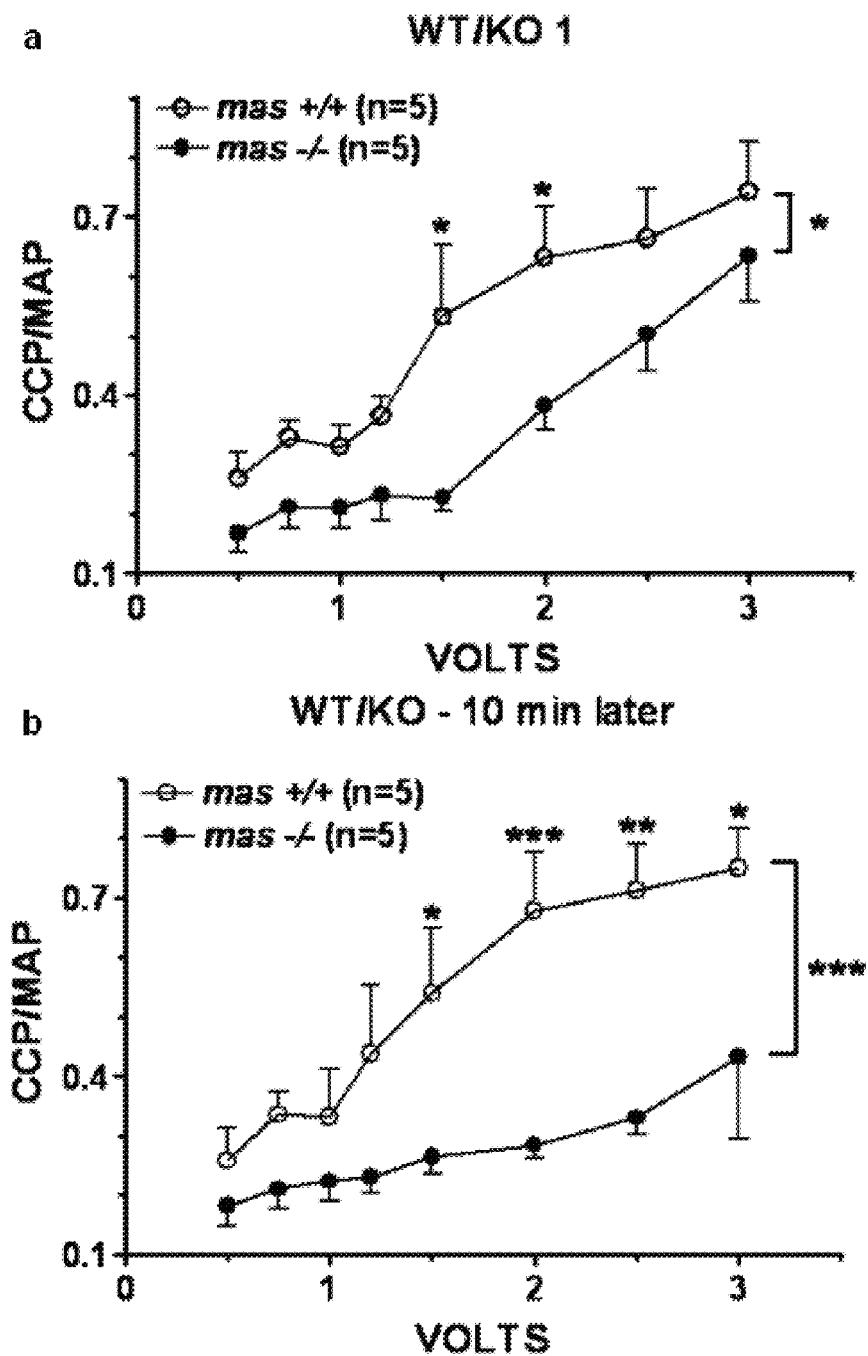
FIG. 7 graphically illustrates the effect of ganglionic nerve stimulation on CCP/MAP of the $Mas^{+/+}$ and $Mas^{-/-}$ mice. a. CCP/MAP rise induced by ganglionic stimulation in $Mas^{-/-}$ mice was significantly lower than in $Mas^{+/+}$. b. CCP/MAP rise induced by a second series of ganglionic stimulation performed 10 min later was further attenuated in $Mas^{-/-}$ than in $Mas^{+/+}$. All results are expressed as mean±s.e.m. ANOVA followed by Bonferroni post hoc test. *, P<0.05,  P<0.01, * P<0.001 compared to $Mas^{+/+}$.
Figure 8:
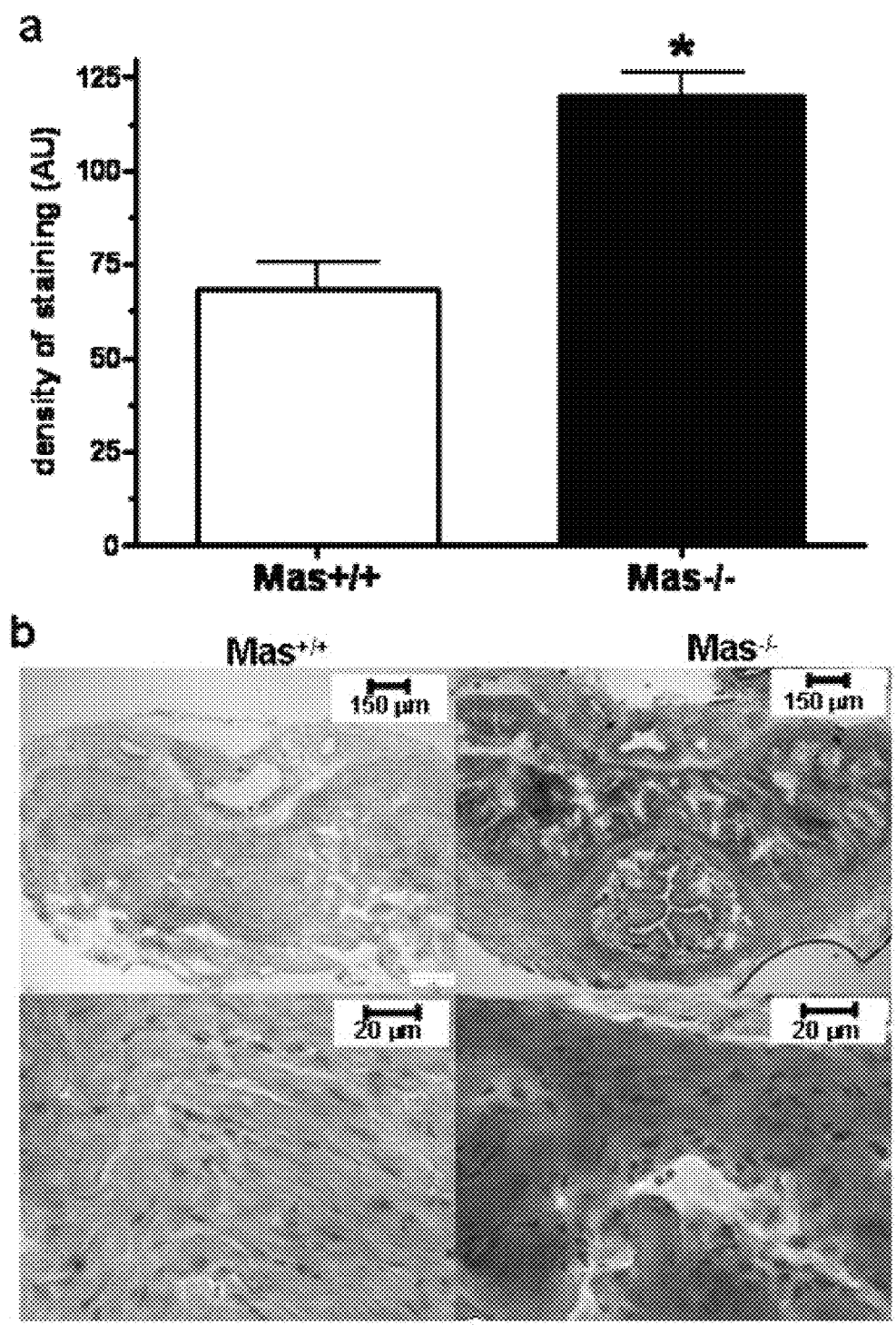
FIG. 8 shows increased fibrous tissue produced by genetic deletion of Mas. a. $Mas^{-/-}$ mice stained with Gomori trichrome showed increasing in fibrous tissue compared to $Mas^{+/+}$ indicating increased collagen content. b. Representative image of Gomori-trichrome staining in $Mas^{+/+}$ and $Mas^{-/-}$ mice corpus cavernosum (4×—high images; 40×—low images). Results expressed as mean±s.e.m, n=4. Unpaired Student t test followed by the Mann Whitney test. P<0.05 compared to $Mas^{+/+}$ mice (AU, arbitrary unit).

The in vivo relevance of the findings of the precedent examples was tested in $Mas^{-/-}$ mice and DOCA-salt hypertensive rats. As shown in FIG. 7 (a-b), electrical stimulation of the $Mas^{-/-}$ MPG induced a change in CCP which was significantly attenuated in comparison with that observed in $Mas^{+/+}$ mice. Because erectile dysfunctions in these animals could be underestimated by the existence of stored nitrosocompounds, a second series of stimulation was performed 10 minutes after the first one. Indeed, the erectile dysfunction becomes markedly evident with a second series of stimulation (see FIG. 7b). As shown in FIG. 8, genetic deletion of Mas leads to a marked increase in fibrous tissue in the penis corpus cavernosum, which probably compromises the erectile function of these animals.

Figure 9:
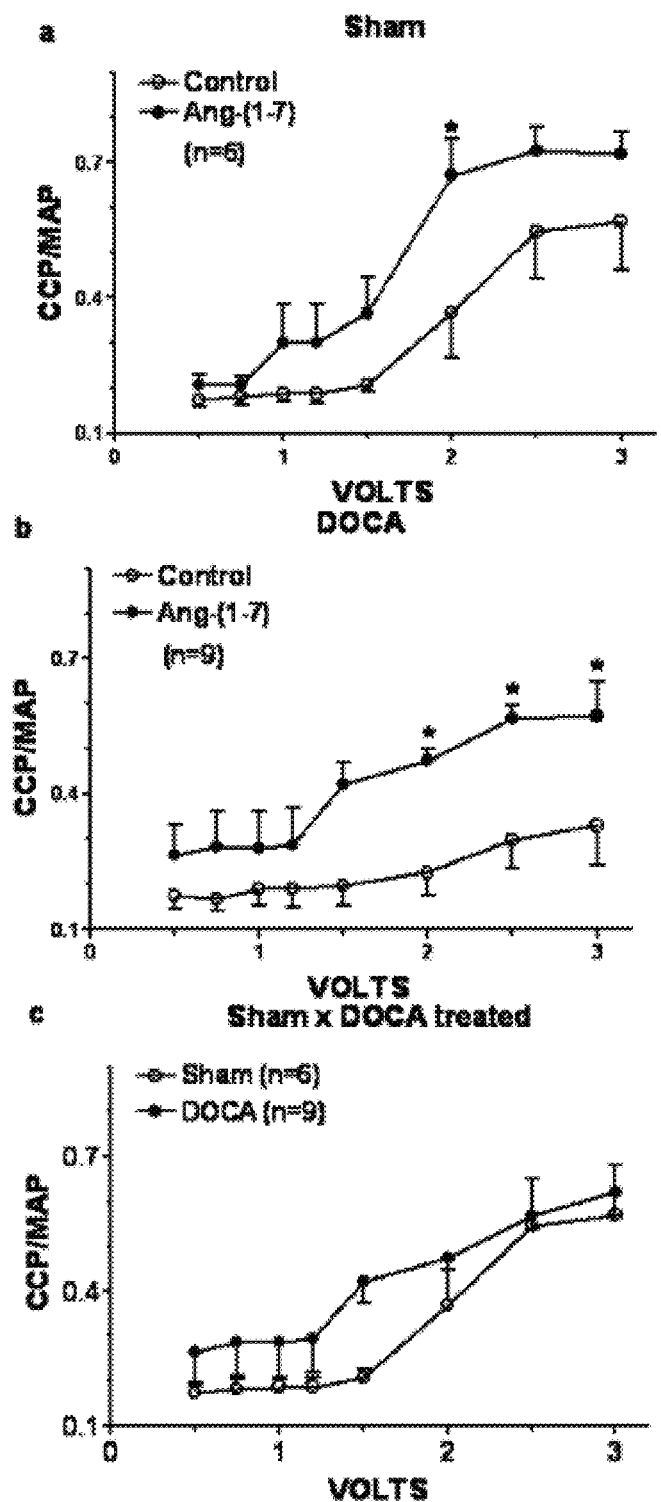
FIG. 9 illustrates the in vivo effect of Ang-(1-7) on normotensive and DOCA-salt hypertensive rats. Treatment with Ang-(1-7) (15.5 pmol/Kg/min body weight) potentiated the voltage-dependent increase in CCP/MAP upon ganglionic stimulation in normotensive rats (a), and normalizes penile function in DOCA-salt hypertensive rats (b-c). All results are expressed as mean±s.e.m. ANOVA followed by Bonferroni post hoc test. *, P<0.05 compared with control, recorded 10 min before drug administration.

In order to test whether Ang-(1-7) could ameliorate ED, its effect was determined in DOCA-salt hypertensive rats (179±4 mmHg vs. 116±2 mmHg; P<0.01) which present severe erectile dysfunction, and a suppressed renin-angiotensin system activity. Doca-salt hypertensive rats showed reduced erectile function in our experimental protocol (2.5 V: 0.55±0.10 vs. 0.30±0.06; 3.0 V: 0.57±0.11 vs. 0.33±0.09, n=8 and 6 for Sham and DOCA, respectively). Local administration of Ang-(1-7) increased the electrically-induced rise of CCP/MAP in both Sham-operated (see FIG. 9a) and DOCA-salt hypertensive rats (see FIG. 9b), normalizing the erectile function of mineralocorticoid hypertensive rats (see FIG. 9c). These data suggest that the facilitatory effect of Ang-(1-7) can be dissociated from its antagonistic activity on AT1-mediated Ang II effects.

Ang-(1-7) acts as a mediator of penile erection by activation of Mas and subsequent eNOS phosphorylation leading to NO release. In the absence of Mas erectile function was severely compromised as demonstrated by penile fibrosis associated to a markedly depressed response to electrical stimulation of the major pelvic ganglion. Furthermore, the severely depressed erectile function of DOCA-salt hypertensive rats was essentially normalized by Ang-(1-7) administration.

The increase in fibrosis observed by antagonizing Ang-1-7 signaling (e.g., deletion of its receptor showed in this example or use of a receptor antagonist) suggests Ang-1-7 can be used to reduce formation of fibrosis in tissues, in particular, penile tissues (e.g., the corpus cavernosum). Another embodiment of this invention is the use of Ang-1-7 to reduce formation of fibrosis in penile tissues for the prevention or treatment of fibrosis-related penile diseases, for example, erectile dysfunction.

Example 6

Preparation of Ang-(1-7) in a Matrix of Hydroxypropyl β-Cyclodextrin

Ang-(1-7) peptide was included in a matrix of hydroxypropyl β-cyclodextrin as described in the U.S. Patent Application 2005/069533. Briefly, the preparation is based on equimolar quantities of Ang-(1-7) and/or an Ang-(1-7) receptor agonist and/or an Ang-(1-7) analogue and a cyclodextrin, e.g. hydroxypropyl β-cyclodextrin. The cyclodextrin component is dissolved in water by using stirring and heating. Then the appropriate amount of Ang-(1-7) is added to the aqueous solution. Following the dissolution, the mixture is frozen in liquid nitrogen and then lyophilized to obtain a dry solid inclusion complex. The resulting product is submitted to physico-chemical characterization by FT infrared spectroscopy, thermal analysis (TG/DTG and DSC), X-ray diffraction and $^1H$, $^{13}C$ NMR spectroscopy and T1 relaxation times, and the expected structure of the Ang-(1-7)/HPβ-CD inclusion complex was confirmed.

Example 7

Absorption and Biological Stability Assays on Ang-(1-7)/HPβ-CD Inclusion Complex Assays for determining absorption and biological stability of the Ang-(1-7)/HPβ-CD inclusion complex were made in aqueous solution. Twelve normal Wistar rats properly prepared were used to carry out the experiments. The animals were divided in 3 experimental groups and subjected to a gavage procedure with a salt solution (0.9%/50 µl) of Ang-(1-7) (100 µg/50 µl) and Ang-(1-7)/HPβ-CD (100 µg/50 µl). Four blood samples (1 ml, each) from the animals were collected. The first collection occurred before gavage procedure, and the remaining three 2, 6 and 24 hours post gavage.

The results demonstrate a complete absorption of Ang-(1-7)/HPβ-CD by the gastrointestinal tract of the animals, with a maximum blood concentration about 6 hours after administration (620±194 pg/ml), and 24 hours after gavage blood concentration levels were reduced to a basal level (30±0.8 pg/ml versus 25±10 pg/ml (before gavage)). When Ang-(1-7) peptide was administered alone, the plasmatic peptide concentration has increased as well, but such an increase was about 8-fold lower than the observed value to Ang-(1-7)/HPβ-CD. In short, the inclusion complex of Ang-(1-7)/HPβ-CD is significantly better absorbed by the gastrointestinal tract as compared with the Ang-(1-7) peptide.

Example 8

Preparation of a Dosage Form of Ang-(1-7)/HPβ-CD+Atenolol

The Ang-(1-7)/HPβ-CD inclusion complex (equimolar ratio) was prepared as described in Example 6. Then, the lyophilized solid was admixed to Atenolol in an amount determined in a basis of a daily dose of 10 mg/kg body weight. The mixture of Ang-(1-7)/HPβ-CD inclusion complex and Atenolol was accomplished by a suitable method well known in the art of pharmacy. Appropriately the resulting mixture is diluted by an appropriate carrier, e.g., those cited herein elsewhere, and the final mixture compressed as tablets or filled in capsules.

Example 9

Evaluating [Ang-(1-7)/HPβ-CD Inclusion Complex+Atenolol] Effect on ED

Eight weeks post-treatment with Ang-(1-7)/HPβ-CD Inclusion Complex and/or Atenolol, the erectile function of the animals (SHR, spontaneously hypertensive rats) was evaluated. Particularly, erectile function of animals chronically treated with Atenolol was evaluated after concurrent administration with Ang-(1-7)/HPβ-CD Inclusion Complex.

The drugs were orally administered via solutions containing them, alone or in combination. As a control, a group of animals was treated with HPβ-CD.

The procedure for inducing erection and intracavernosal pressure measurement was made as previously described (see, T. M. Mills, R. W. Lewis, V. S. Stopper, *Biol Reprod* 59, 1413 (December, 1998). Firstly, the animals (SHR) were anesthetized with intraperitoneal urethane (140 mg/kg) and placed on a thermal plate to maintain body temperature at 37° C. A polyethylene cannule was introduced into the animal trachea to keep respiratory patency. Following, the rat left femoral artery was cannulated with a polyethylene tube (PE-50) with heparinized saline (200 U/ml) for continuous monitoring of mean arterial pressure (MAP). The catheter was connected to a pressure transducer. The penial erection was obtained by applying electric stimulation on the major pelvic ganglion (MPG). To evaluate the effects of the ganglionic-stimulated changes in CCP (corpus cavernosum pressure)/MAP (mean arterial pressure), the nerve was stimulated with range of voltages (0.5, 0.75, 1.0, 1.2, 1.5, 2.0, 2.5 and 3.0 V, 5 msec pulses at a frequency of 12 Hz). Following, rat left corpus cavernosum was cannulated with 30-gauge needles attached to a computer data acquisition system via short lengths of polyethylene (PE)-tubing 10 containing heparinized saline (200 U/ml). The results are presented as a CCP/MAP ratio from the function of voltages employed for stimulating the MPG according to the proposed sequence range.

Figure 10:
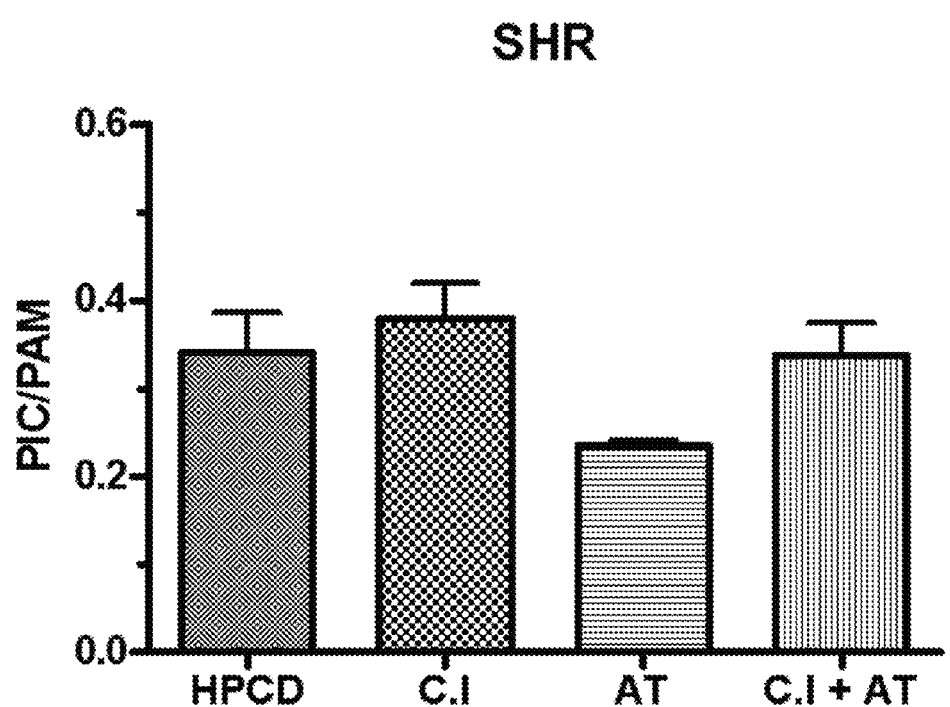
FIG. 10 illustrates the effect on erectile function of SHR chronically treated with Ang-(1-7)/HPβ-CD Inclusion Complex and Atenolol. The treatment of the animals with Atenolol reduced the CCP/MAP rise which was induced by ganglionic electric stimulation (1.5 V, 5 msec pulses at a frequency of 12 Hz). The Ang-(1-7)/HPβ-CD Inclusion Complex did not alter the CCP/MAP rise, but annulled the attenuating effect induced by Atenolol on erectile function.

FIG. 10 clearly shows that Atenolol has reduced the intracavernal pressure rise which was induced by the stimulation on the major pelvic ganglion with a maximum voltage of 1.5V. SHR animals chronically treated with the Ang-(1-7)/HPβ-CD inclusion complex did not present intracavernosal pressure parameters altered. Notwithstanding, the Ang-(1-7)/HPβ-CD inclusion complex annulled the attenuating effect induced by Atenolol on erectile function of animals chronically treated with such a β-blocker.

The present invention is not limited to the description of the embodiments above, but may be altered by a skilled person within the scope of the claims. An embodiment based on a proper combination of technical means disclosed in different embodiments is encompassed in the scope of the present invention. Variations may be made and should not to be regarded as a departure from the spirit and scope of the invention, and all such modifications as would be obvious to one skilled in the art are intended to be included within the scope of the following claims. The disclosed specific embodiments and examples of implementation serve solely to illustrate the technical details of the present invention, which should not be interpreted only within the limits of such embodiments and accomplished examples, but rather may be applied in many variations within the spirit of the present invention, provided such variations do not exceed the scope of the patent claims set forth below.

The invention claimed is:

1. A method for treating erectile dysfunction in an individual in need of such a treatment, said method comprising administering to said individual an effective amount of Angiotensin-(1-7) and/or an Angiotensin-(1-7) receptor agonist, alone or in combination with other active ingredients, to decrease the symptoms of erectile dysfunction.

2. The method according to claim 1, wherein the amount of Angiotensin-(1-7) and/or an Angiotensin-(1-7) receptor agonist, is effective to maintain a systemic blood pressure in levels that do not cause sexual dysfunction.

3. The method according to claim 1, wherein the Angiotensin-(1-7) is a hydroxypropyl β-cyclodextrin-Ang-(1-7) Inclusion Complex.

4. A method for restoring erectile capacity in an individual in needs of such a treatment, said method comprising administering to said individual an effective amount of Angiotensin-(1-7) and/or an Angiotensin-(1-7) receptor agonist, alone or in combination with other active ingredients, to restore erectile capacity.

5. The method according to claim 4, wherein the amount of Angiotensin-(1-7) and/or an Angiotensin-(1-7) receptor agonist, is effective to revert erectile dysfunction caused by hypertension treatment with anti-hypertensive agents.

6. The method according to claim 5, wherein the anti-hypertensive agent is a β-blocker compound.

7. The method according to claim 6, wherein the β-blocker compound is atenolol.

8. The method according to claim 7, wherein the Angiotensin-(1-7) is a hydroxypropyl β-cyclodextrin-Ang-(1-7) Inclusion Complex, which is combined with a β-blocker compound.

9. The method according to claim 8, wherein the β-blocker compound is atenolol.

10. The method according to claim 1, wherein the amount of Angiotensin-(1-7) and/or an Angiotensin-(1-7) receptor agonist, and/or an Angiotensin-(1-7) analogue is effective to maintain intracavernosal pressure to a level substantially close to the mean arterial pressure.

* * * * *